United States Patent
Linkwitz et al.

(10) Patent No.: US 6,295,469 B1
(45) Date of Patent: *Sep. 25, 2001

(54) FORMULATION FOR ELECTRICALLY ASSISTED DELIVERY OF LIDOCAINE AND EPINEPHRINE

(75) Inventors: Andreas Linkwitz, San Carlos; Ivan W. Chin, Belmont, both of CA (US); J. Richard Gyory, North Oaks, MN (US); Ronald V. Thompson, Coon Rapids, MN (US); Paul J. Urbanski, Minneapolis, MN (US)

(73) Assignee: Alza Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/970,697

(22) Filed: Nov. 14, 1997

(51) Int. Cl.[7] .................................................. A61N 1/30
(52) U.S. Cl. .................................................. 604/20
(58) Field of Search ........................... 604/20, 49, 890.1; 607/115, 62

(56) References Cited

U.S. PATENT DOCUMENTS

| | | | |
|---|---|---|---|
| 4,141,359 | 2/1979 | Jacobsen et al. | 128/172.1 |
| 4,474,570 | 10/1984 | Ariura et al. | 604/20 |
| 4,764,164 | * 8/1988 | Sasaki | 604/20 |
| 5,006,108 | 4/1991 | LaPrade | 604/20 |
| 5,019,034 | * 5/1991 | Weaver et al. | 604/20 |
| 5,047,007 | 9/1991 | McNichols et al. | 604/20 |
| 5,131,403 | 7/1992 | Haynes | 128/760 |
| 5,135,479 | 8/1992 | Sibalis et al. | 604/20 |
| 5,224,927 | 7/1993 | Tapper | 604/20 |
| 5,224,928 | 7/1993 | Sibalis | 604/20 |
| 5,246,418 | 9/1993 | Haynes et al. | 604/20 |
| 5,261,903 | 11/1993 | Dhaliwal et al. | 604/416 |
| 5,302,172 | 4/1994 | Sage, Jr. et al. | 604/20 |
| 5,306,235 | * 4/1994 | Haynes | 604/20 |
| 5,314,502 | 5/1994 | McNichols | 604/20 |
| 5,320,597 | 6/1994 | Sage, Jr. et al. | 604/20 |
| 5,334,138 | 8/1994 | Sage, Jr. et al. | 604/20 |
| 5,358,483 | 10/1994 | Sibalis | 604/20 |
| 5,540,669 | 7/1996 | Sage, Jr. et al. | 604/290 |
| 5,562,607 | 10/1996 | Gyory | 604/20 |
| 5,563,153 | 10/1996 | Mueller et al. | 514/305 |
| 5,688,233 | * 11/1997 | Hofmann et al. | 604/20 |
| 5,695,459 | * 12/1997 | Meguro | 604/20 |
| 5,843,016 | * 12/1998 | Lugnani et al. | 604/21 |

FOREIGN PATENT DOCUMENTS

| | | | |
|---|---|---|---|
| 981182 | 1/1976 | (CA) . | |
| 0 292 930 | 11/1988 | (EP) | A61N/1/30 |
| 2 239 803A | 7/1991 | (GB) | A61N/1/30 |
| WO 91/11182 | 8/1991 | (WO) . | |
| WO 93/10854 | 6/1993 | (WO) | A61N/1/30 |

OTHER PUBLICATIONS

Grubstein, et al.: "Stabilization of Epinephrine in a Local Anesthetic Injectable Solution Using Reduced Levels of Sodium Metabisulfite and EDTA", Drug Development and Industrial Pharmacy, vol. 18 (14), pp. 1549–1566, (1992), XP002056303.

(List continued on next page.)

Primary Examiner—Richard K. Seidel
Assistant Examiner—Michael J Hayes
(74) Attorney, Agent, or Firm—Owen Bates; D. Byron Miller

(57) ABSTRACT

The invention relates to formulations for the electrically assisted transdermal delivery of lidocaine and epinephrine. The present invention further provides methods and devices for the electrically assisted delivery of local anesthetics, preferably lidocaine.

18 Claims, 8 Drawing Sheets

FOREIGN PATENT DOCUMENTS

Comeau, Maurice et al., Arch Otolarynol./vol. 93, Aug. 1973, Iontophoresis, "Local Anesthesia of the Ear by Iontophoresis", pp 32–38.

Russo, John Jr., et al., American Journal of Hospital Pharmacy, vol. 37, Jun. 1980, pp 843–847, "Lodocaine Anesthesia: Comparison of Iontophoresis, Injection, and Swabbing".

Arvidsson, S.B.,et al., Amnesthesiol. Scand 1984: vol. 28, pp. 209–210, "Painless Venipuncture. A Clinical Trial of Iontophoresis of Lidocaine for Venipuncture in Blood Donors".

News Bulletin, Iomed Inc., 2 pp .

Physicians'Desk Reference, 50 Ed., 1996, pp 567–570.

F–D–C Reports, vol. 58, No. 1, 2 pp.

\* cited by examiner

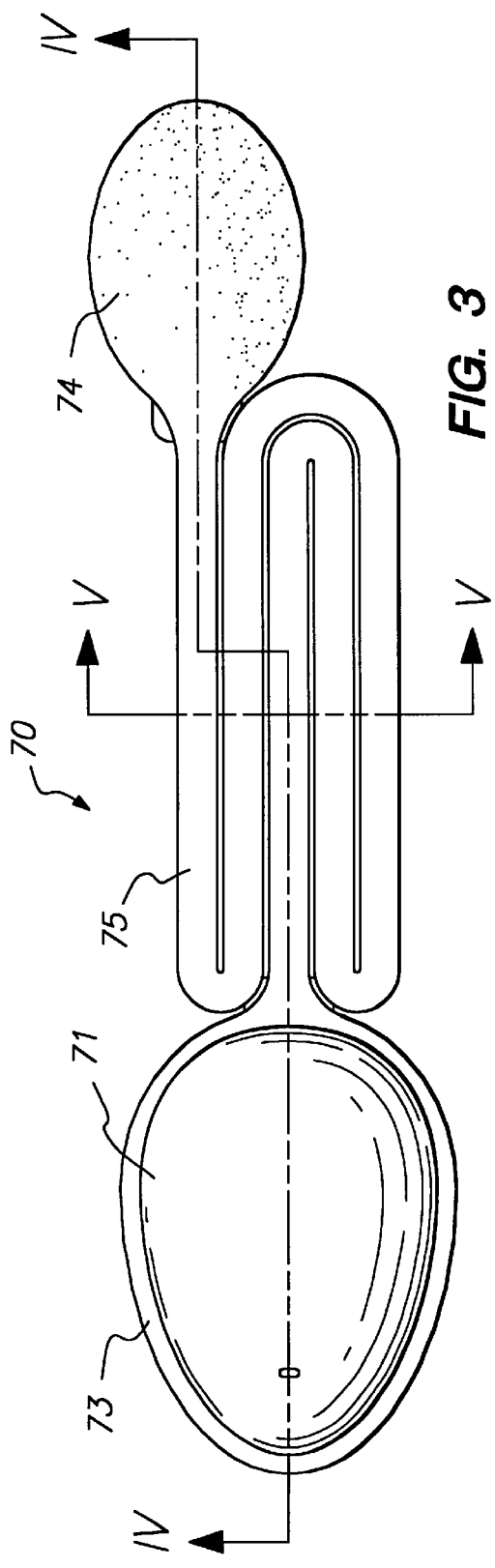
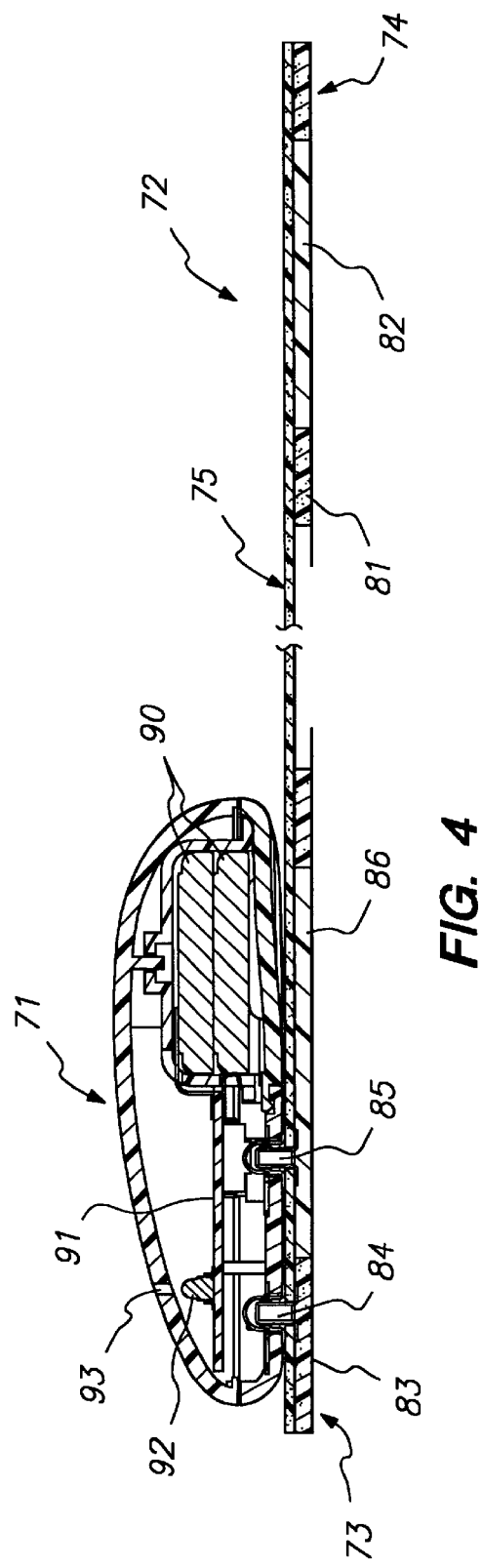
FIG. 3
FIG. 4

FORMULATION FOR ELECTRICALLY ASSISTED DELIVERY OF LIDOCAINE AND EPINEPHRINE

TECHNICAL FIELD

The present invention relates to non-invasive, electrically-assisted delivery of lidocaine through a body surface such as intact skin.

BACKGROUND ART

Anesthetics are drugs which produce anesthesia, a condition characterized by the inability to appreciate sensation. Two types of anesthesia are generally recognized: local anesthesia and general anesthesia. In local anesthesia, the anesthesia is confined to a portion of the body, whereas in general anesthesia, the anesthesia extends to the entire body.

Local anesthetics reversibly block impulse conduction in peripheral nervous tissue, thereby producing a transient loss of sensation in a circumscribed area of the body without causing a general loss of consciousness. This action can be used to block pain sensation to a specific area of the body. Hence, local anesthetics are used to prevent pain in surgical procedures, dental manipulations, injury and disease.

Lidocaine is a local anesthetic which may be applied topically, for example, to mucous tissues. However, its effectiveness as a topical anesthetic is limited by its low adsorption rate (via passive diffusion) through the skin; the salts of lidocaine do not diffuse through intact skin to any appreciable degree, whereas the base forms of lidocaine diffuse through intact skin only to a limited degree.

The hydrochloride salt form of lidocaine (lidocaine HCl) is also widely used as a local anesthetic and is normally administered via injection. However, systemic absorption of lidocaine can lead to adverse side effects such as drowsiness, confusion, nausea, seizures and coma. These side effects are aggravated by the vasodilating effect of lidocaine, which increases the rate of its absorption into the systemic blood circulation.

Systemic absorption can be reduced by the addition of a vasoconstrictor. For example, the presence of epinephrine helps retard adsorption of lidocaine, thereby reducing its systemic toxicity. Epinephrine has other desirable effects as well. For example, it may be desirable to increase the duration of the drug's local anesthetic effect. The duration of action of lidocaine, as with any local anesthetic, is proportional to the time during which it is in actual contact with nerve tissues. The vasoconstrictive effect of epinephrine maintains localization of lidocaine at the nerve thereby prolonging the drug's anesthetic effect, increasing the duration of action of lidocaine, as well as increasing its efficiency by decreasing the volume of solution required to achieve an anesthetic effect. In addition to reducing the systemic absorption of lidocaine, epinephrine acts to reduce bleeding at the site of the (i.e., subsequent) surgical procedure.

However, epinephrine is difficult to work with as it is rapidly degraded in the presence of oxygen (U.S. Pat. No. 5,334,138). Moreover, the addition of epinephrine to hydrochloric solutions of lidocaine reduces the storage stability of the anesthetic solution (WO 91111182).

In addition to problems associated with the side effects of lidocaine, local injection of the drug can be painful, particularly in sensitive areas of the body such as the face.

Although iontophoresis has been used as a painless and effective method to deliver lidocaine into the skin (Comeau et al., Arch Otolaryngol 98:114–120 (1973)), as with administration by injection, removal of lidocaine by the vasculature and subsequent systemic adsorption can result in toxic side effects. Although the use of vasoconstrictors to reduce adsorption of iontophoretically delivered drugs has been suggested, instability of epinephrine remains problematic (U.S. Pat. No. 5,334,138).

Thus, a need exists for stabilized formulations of lidocaine as well as non-invasive, convenient means of administering lidocaine which result in increased localized anesthetic effect of the drug.

DISCLOSURE OF THE INVENTION

The present invention relates to the electrically assisted transport of lidocaine and epinephrine. Specifically, the invention provides compositions for the electrically assisted delivery of lidocaine and epinephrine. Preferably, the compositions comprise about 1–10% lidocaine and about 0.01–0.2% epinephrine. In a preferred embodiment, both lidocaine and epinephrine are positively charged. Preferably, the compositions comprise lidocaine HCl and epinephrine bitartrate.

The compositions preferably further comprise one or more anti-oxidants, metal chelators or other agents, which deter microbial growth and enhance the stability of the epinephrine. Preferably, the antioxidant is sodium metabisulfite. Preferably, the metal chelator is edetate bisodium dihydrate.

The present invention further provides an electrotransport delivery device for delivering one or more agents, preferably a local anesthetic, and preferably lidocaine, by electrotransport through a body surface such as skin. The device comprises a pair of electrode assemblies, at least one of the assemblies comprising the agent to be delivered, and a source of electrical power adapted to be electrically connected to the pair of electrode assemblies. The device comprises a circuit means connecting the pair of electrode assemblies and the source of electrical power, the circuit means comprising an activation circuit and a current generating circuit. The activation circuit, which comprises a body surface resistance detection circuit and a current pulsing circuit, is electrically connected to the power source. The activation circuit is responsive to the completion of a circuit between the electrode assemblies, wherein upon completion of the circuit, the resistance detection circuit detects the resistance between the electrode assemblies (i.e., the electrical resistance of the body surface). Where the resistance is equal to or greater than a pre-determined threshold value, a pulsed voltage is delivered across the electrode assemblies which is effective to reduce the resistance of the body surface to a value less than the threshold value. Where the resistance is less than the threshold value, whether initially or as a result of being lowered by delivery of pulsed voltage, the activation circuit activates the current generating circuit. The generating circuit is electrically connected to the activation circuit for generating current for delivering the agents and is selectively activatable by the activating circuit. The activation circuit draws substantially no power consumption when the circuit between the electrodes assemblies is open, while the current generating circuit draws substantially no power consumption when not activated.

BRIEF DESCRIPTION OF THE DRAWINGS

FIG. 3 is a top view of the device shown in FIG. 1.

FIG. 4 is a sectional view of the device shown in FIGS. 1–3, taken along line IV—IV in FIG. 3.

MODES FOR CARRYING OUT THE INVENTION

Figure 1:
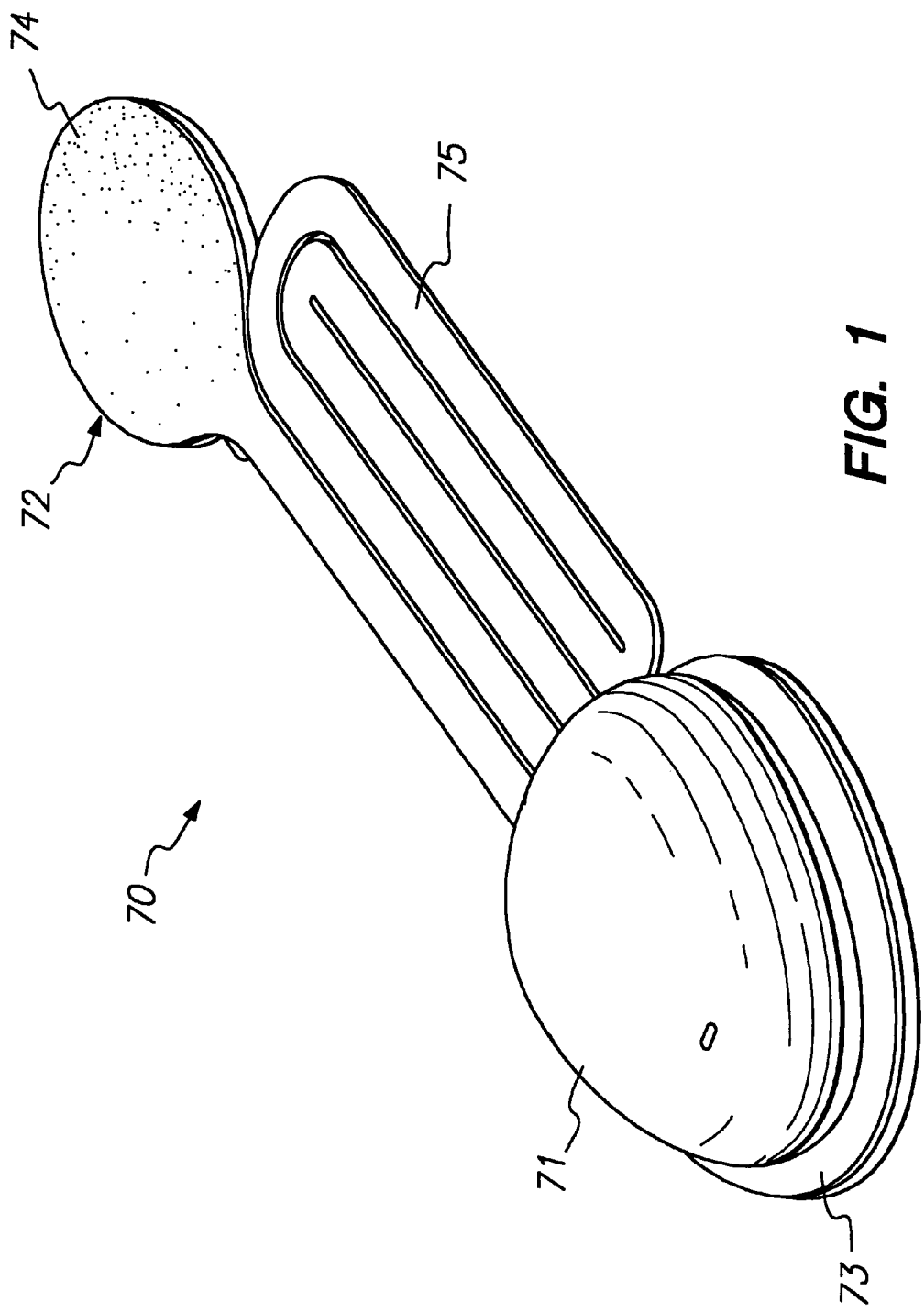
FIG. 1 is a perspective view of a preferred electrotransport device for delivering lidocaine and epinephrine.

The present invention provides compositions for the electrically assisted transdermal delivery of lidocaine and epinephrine, preferably comprising about 1–10% lidocaine and about 0.01–0.2% epinephrine. In a preferred embodiment of the invention, the compositions comprise about 1–5% lidocaine and about 0.025–0.075% epinephrine, and more preferably, about 2–3% lidocaine and about 0.04–0.06% epinephrine. Although the use of epinephrine is preferred, other pharmaceutically acceptable agents which possess vasoconstrictive properties may be used.

As used herein the terms "electrically assisted delivery" or "electrotransport" generally refer to the delivery of an agent, such as a drug, through a membrane, such as skin, mucous membrane or nails. The delivery is induced by application of an electrical potential. Electrotransport may occur via electromigration, also known as iontophoresis; electroosmosis or electroporation, or any combination thereof. The terms thus include the electrically induced or enhanced transport of one or more agents, which may be charged, uncharged, or mixture thereof via whatever specific mechanism by which the agent is actually transported.

As used herein the terms "iontophoretic" and "iontophoresis" refer to the delivery of ionic agents into the body by means of an electric current.

As the electrically assisted delivery of an agent is facilitated where the active agent is charged, it is preferred that the compositions of the present invention comprise ionizable salt forms of lidocaine and epinephrine. Active agent modification for iontophoretic delivery is guided by well-known procedures. Typically, the basic (OH⁻ or amine) or acid (H⁺) form of the agent is made, depending on whether the anionic (negatively charged ion) or cationic (positively charged ion) form of the active agent is to be delivered. Common modifications of active agents include modification to a halide salt form. For example, to deliver a positively charged drug, the chloride or hydrochloride salt form of the agent can be made. Likewise, the composition is typically dissolved in a suitable solvent to obtain the ionic form for delivery. Suitable solvents include polar liquids such as water, glycerine, and lower alkyl alcohols such as methyl alcohol, ethyl alcohol and branched alcohols such as isopropyl alcohol. In a preferred embodiment, the solvent is water. The compositions may comprise about 50–95% water, preferably about 60–90% water.

Thus, for example, to facilitate the transport of lidocaine, it is preferred that the compositions comprise a charged, preferably positively charged, pharmaceutically acceptable form of lidocaine. In a preferred embodiment, the compositions comprise lidocaine HCl.

Similarly, a modified, pharmaceutically acceptable form of epinephrine is preferred, preferably a pharmaceutically acceptable salt of epinephrine, such as the HCl and borate salt forms. In a preferred embodiment of the invention, the compositions comprise the bitartrate salt of epinephrine.

It is preferred that the composition is maintained at a pH that allows lidocaine and epinephrine to be positively charged. It has been determined that epinephrine and lidocaine are positively charged at pH levels up to approximately 8. However, epinephrine is not stable at higher pH levels. On the other hand, low pH levels may have an effect on patient comfort. In addition, at low pH's drug delivery efficiency is compromised by the increased concentration of H⁺ ions which compete with lidocaine and epinephrine. Therefore, the pH is preferably maintained in the range of 3–5. The composition may comprise a buffer to maintain pH level, such as a citric acid/citrate buffer.

The compositions preferably further comprise one or more anti-oxidants, metal chelators or similar agents, which deter microbial and/or fungal growth and which serve to enhance the aqueous stability of the epinephrine. In a preferred embodiment of the invention, the compositions comprise both an antioxidant, preferably about 0.01–0.2%, more preferably about 0.03–0.13%, and most preferably about 0.05–0.10%; and a metal chelator, preferably about 0.06–0.25%, more preferably about 0.10–0.15%, and most preferably about 0.12–0.14%. Preferably, when used in combination with positively charged forms of lidocaine and epinephrine, the antioxidants and metal chelators are negatively charged to minimize their migration from the anodic reservoir into the patient. According to a preferred embodiment of the invention, the antioxidant is sodium metabisulfite, and the metal chelator is edetate bisodium dihydrate.

The compositions may optionally comprise other antimicrobial agents, such as cetylpyridinium chloride, benzoic acid, sorbic acid, methyl or propyl paraben or other agents known in the art.

The compositions preferably further comprise a suitable matrix for holding the liquid drug solution. In the case of an aqueous drug solution, the matrix is preferably a hydrophilic polymer or gel matrix. Although hydrophobic polymers may be used, hydrophilic polymers are preferred since hydrophilic polymers have a relatively high equilibrium water content, water being the preferred ion transport medium. Suitable hydrophilic polymers include copolyesters such HYTREL® (DuPont De Nemours & Co., Wilmington, Del.), polyvinylpyrrolidones, polyvinyl alcohol, polyethylene oxides such as POLYOX (Union Carbide Corp.), CARBOPOL® (BF Goodrich, Akron, Ohio), blends of polyoxyethylene or polyethylene glycol with polyacrylic acid such as POLYOX blended with CARBOPOL®, polyacrylamide, KLUCEL®, cross-linked dextran such as SEPHADEX® (Pharmacia, Uppsala Sweden), WATER LOCK® (Grain Processing Corp., Muscatine Iowa), which is a starch-graft-poly(sodium acrylateco-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Patent Development Corp.), natural gums, chitosan, pectin, starch, guar gum, locust bean gum, and the like, and blends thereof. Other suitable hydrophilic polymers can be found in Scott et al., Handbook of Common Polymers (CRC Press, 1971). In a preferred embodiment of the invention, the composition comprises 12–24% hydrophilic gel, preferably, polyvinyl alcohol. Preferably, the polyvinyl alcohol is of average molecular weight of about 10K to 100K Da, and more preferably, 20K to 70K Da. Preferably, the polyvinyl alcohol is hydrolyzed, preferably 80–100%, and more preferably, 90–100% hydrolyzed.

Optionally, the composition may comprise a hydrophobic polymer. Suitable hydrophobic polymers include polyisobutylenes, polyethylene, poylpropylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohols such as n-butanol, 1-, 2- or 3-methyl pentanol, 2-ethyl butanol, isooctanol, n-decanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, itaconic acid, N-branched ($C_{10}$–$C_{24}$) alkyl maleamic acids, glycol diacrylates, and blends thereof.

The compositions may further comprise other components commonly used in the art of electrotransport, provided that such components do not significantly or adversely affect the properties of lidocaine or epinephrine or its ability to be iontophoretically delivered. For example, it is preferred that extraneous positive ions are minimized in order to maximize the delivery efficiency of the active agents.

It will be appreciated that the amount of lidocaine and epinephrine transported through the skin or tissue will depend on many factors such as the charge of the agents, the relative migration rates of the agents, the amplitude of the applied electrotransport current, the solution concentration, pH, duration of iontophoresis, the presence of competitive ions in the composition, and area of electrode contact, as well as various factors affecting the resistance of a patient's skin or tissue such as skin thickness, regional blood flow, quantity of hair follicles and sweat glands, etc., and will ultimately be at the discretion of the attendant physician or clinician.

However, it is preferred that the amount of lidocaine and epinephrine delivered and the rate of delivery is effective to achieve a local anesthetic effect in less than 20 minutes, preferably in 15 minutes or less. Thus, the device is preferably applied to a patient's skin or tissue for a period of about 5 to 20 minutes, preferably 15 minutes or less. In a more preferred embodiment, the device is applied for about 10 minutes.

The active agents can be delivered using any suitable electrotransport mechanism or device. Typically, electrotransport devices use at least two electrodes that are in electrical contact with some portion of the skin, nails, mucous membrane or other surface of the body. One electrode, commonly called the donor or active electrode, is the electrode from which the agent is delivered into the body. The other electrode, typically termed the counter or return electrode, serves to close the electrical circuit through the body. For example, if the agent to be delivered is positively charged, i.e., a cation, then the anode is the active or donor electrode, while the cathode serve to complete the circuit. Alternatively, if an agent is negatively charged, i.e., an anion, the cathode is the donor electrode. Additionally, both the anode and cathode may be considered donor electrodes if both anionic and cationic agent ions, or if uncharged or neutrally charged agents, are to be delivered. Thus, for example, in accordance with the preferred embodiment of the invention, i.e., where the composition comprises lidocaine HCl and epinephrine bitartrate, the anode is the donor electrode.

In a preferred embodiment, the size of the anode is chosen so that drug delivery and hence anesthetic effect is limited to the site of the subsequent surgical procedure and the effected surrounding area. For example, where the surgical site is small, such as in the case of mole removal, it is preferred that the size of the anode be minimized so that the current delivered per unit area of tissue (i.e., current density) is increased. This increases the drug delivery density, limits the anesthetic effect to only those tissues effected by the surgical procedure, and decreases the time required to achieve the requisite anesthetic effect. Patient discomfort normally associated with increased current densities is minimized by the delivery of lidocaine. It is further preferred that cathode size be large relative to the anode so that current density is minimized, thereby decreasing patient discomfort at the cathode site.

Electrotransport delivery systems generally require at least one reservoir or source of the agent to be delivered, which is typically in the form of a liquid solution or suspension held in a gel or other hydrophilic polymer as discussed hereinbefore.

The reservoir associated with the counter electrode (according to the preferred embodiment, the cathode) may optionally comprise a buffer solution to maintain pH levels. It has been found that the use of buffers comprising multivalent ions tends to minimize patient discomfort at the site of the cathode. Thus, it is preferred that where a buffer is to be used in a counter electrode reservoir, the buffer system comprise multivalent ions, preferably with a valence of ±2 or ±3. In a preferred embodiment, the counter electrode reservoir comprises a phosphate buffer, preferably comprising about 0.1–2.0% sodium phosphate monohydrate and 0–2.0% sodium chloride. The counter electrode reservoir may further comprise one or more preservatives, antioxidants or metal chelators, preferably positively charged to minimize migration from the cathodic counter reservoir into the patient.

The donor reservoir is electrically connected to, and positioned between, the donor electrode and the body surface, to provide a fixed or renewable source of one or more agents or drugs. Electrotransport devices also have an electrical power source such as one or more batteries. Typically, one pole of the power source is electrically connected to the donor electrode, while the opposite pole is electrically connected to the counter electrode. The electrotransport device may also have an electrical controller that controls the current applied through the electrodes, thereby regulating the rate of agent delivery.

All electrotransport agent delivery devices utilize an electrical circuit to electrically connect the power source and the electrodes. These circuits range from the use of simple conductive connections (U.S. Pat. No. 4,474,570) to the use of more complex electrical components to control the amplitude, polarity, timing, waveform shape, etc. of the electric current supplied by the power source (U.S. Pat. No. 5,047,007).

According to one embodiment, the circuitry is designed to increase the current gradually in a step-wise manner. Gradually increasing amounts of lidocaine are thus delivered which serve to desensitize the site of drug delivery in the early stages of system application and reduce patient discomfort associated with higher current density levels (e.g., above 100 $\mu A/cm^2$) of the applied electrotransport current.

In a preferred embodiment, the circuitry is designed to increase the current to its operating level in 2 or 3 steps. For example, the current profile may be designed so that an initial current density of 25 $\mu A/cm^2$ is delivered for the first 15 seconds of electrotransport current application, 125 IAcm$^2$ for the next 30 seconds, and increased thereafter to the chosen operating current density.

The device may further comprise an electrical circuit, for example, an internal switch, such that current is not drained from the power source while the device is not in use (U.S. Pat. No. 5,562,607). Preferably, the internal switch need not be manually activated but rather is automatically activated at the time of use. Thus, the circuitry is designed to detect when the device is in contact with a patient's skin. Devices comprising such automatic switches are described in U.S. Pat. No. 5,314,502. Such circuits comprise an activation circuit and a current generating circuit. The activation circuit is electrically connected to the power source and is responsive to the completion of a circuit between the electrode assemblies, for example, by applying the electrodes to a body surface. Upon closing the circuit between the electrode assemblies, the activation circuit automatically activates the current generating circuit. The current generating circuit then generates an electric circuit suitable for delivering the drug or agent.

As one of skill in the art will appreciate, the resistance of the skin drops dramatically as even a very low level of current is applied. Thus, the resistance of skin, which may initially have been 1 Megaohm or greater, decreases to approximately 5 to 10 kohms after electrotransport current has been applied to the skin site for several minutes. At these initially high skin resistance levels, the compliance voltage of the device (i.e., the highest voltage level applied by the device) may be insufficient to deliver the desired current level. As drug delivery rate is dependent upon the applied level of electrotransport current, the electrotransport flux of the drug in these instances, falls below the desired level at least until the skin resistance is sufficiently lowered. It may be desirable in certain circumstances, such as where the application time is intended to be brief, to initiate treatment shortly (e.g., within seconds) after application of the device to the skin. Thus, the device may comprise an activation circuit which further comprises a means for lowering the resistance of the skin upon applying the device to the skin. For example, the circuit may comprise a means for applying short pulses of low level electrical current to reduce skin resistance to a predetermined level at which time the treatment phase is activated. The circuitry may further comprise a means for shutting down the device where resistance is not lowered to this predetermined level (e.g., because the device is not in contact with a patients skin).

Preferably, the circuitry is designed to detect the resistance between the anode and cathode prior to delivery of the low level current, by applying a short high voltage pulse (e.g., 20 volts) across the electrodes. If the resistance across the electrodes is less than a predetermined threshold resistance value, then the treatment phase is initiated. If the resistance is greater than this threshold value, then the circuitry applies short high voltage pulses across the electrodes which act to lower the skin resistance to a level at which treatment can be initiated.

Figure 6:
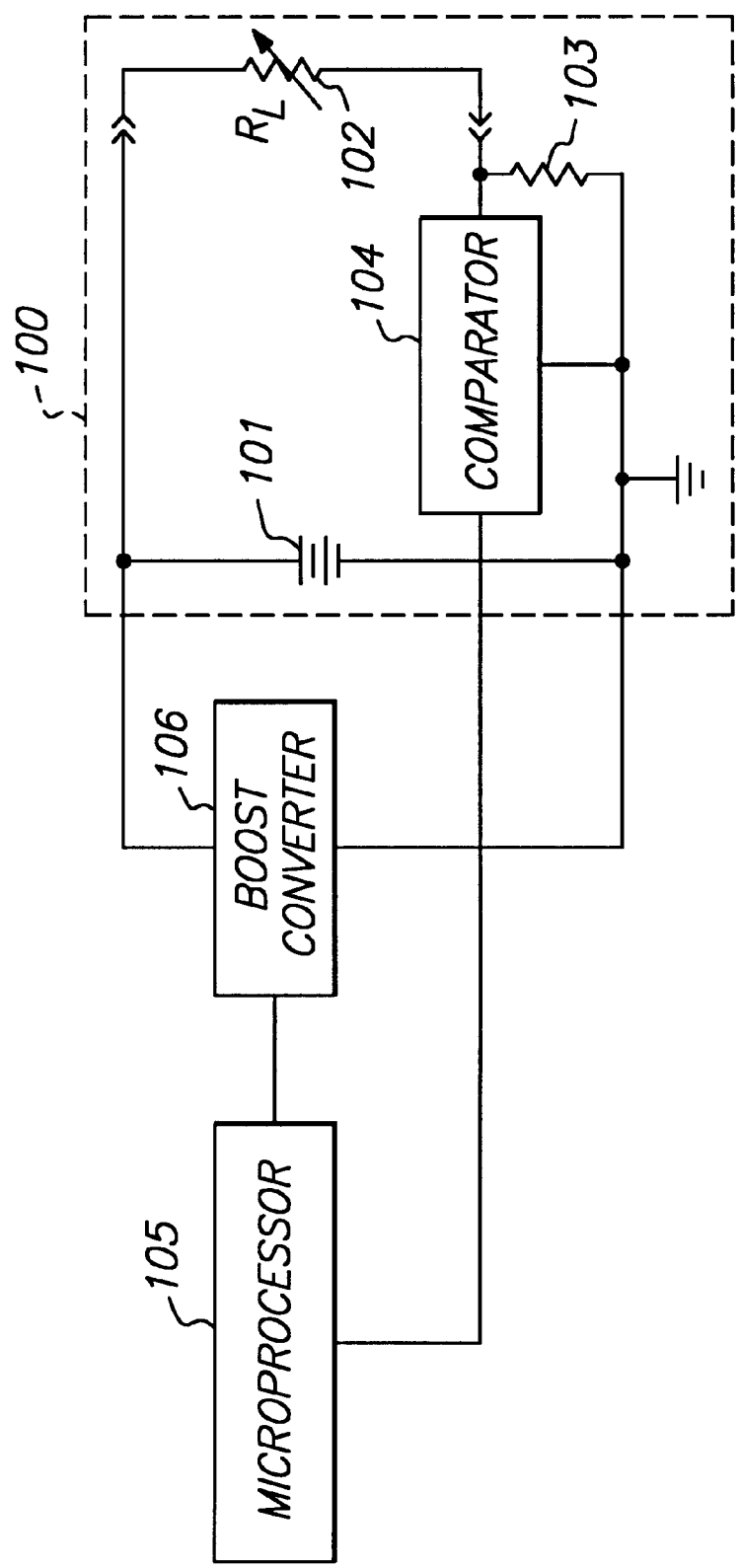
FIG. 6 is a schematic of an electronic circuit for an electrotransport delivery device according to the present invention.

Referring to FIG. 6, there is shown, by way of example only, a resistance detection circuit that may be integrated into the activation circuit described above. Basically, the resistance detection circuit 100 comprises a power source 101, a variable resistor 102 (i.e., the patient's skin when the electrode assemblies are in contact with the patient's skin or tissue), resistor 103 and a comparator 104. The circuit further comprises a microprocessor 105 and a DC—DC boost converter 106. When the device is first placed on the patient, a switch is closed and the device powers up. A path is established for current flow from power source 101 through the patient's skin (variable resistor 102) to ground. The voltage is divided between variable resistor 102 and resistor 103. If the voltage across resistor 103 is not high enough to trip comparator 104, microprocessor 105 will turn on the DC—DC boost converter 106 for a timed interval. This increases or boosts the voltage across resistors 102 and 103. The output of comparator 104 is checked at the beginning and end of this voltage boost. If no load (i.e., current) is detected, microprocessor 105 waits and checks again. If no load is detected, the DC—DC boost converter 106 is turned on again. This process is repeated until the resistance is sufficiently lowered, or for a desired period of time. If no load is detected at the end of this period of time, the device powers down and alerts the caregiver, via for example an LED.

The boosted voltage can be any amount effective to lower the resistance of the body surface to which the device is applied, although it has been found that higher voltages are more effective in lowering resistance. Generally, the boosted voltage will be greater than the voltage of power source. However, in the interest of patient comfort, it is preferred that the voltage not exceed about 24 V.

As will be appreciated, the duration of the boosted voltage and time between boosts may be varied. According to a preferred embodiment of the invention, boosts are delivered for 1 second, and the time between consecutive boosts is about 3 seconds. It has been found that current delivered in this manner can result in drug treatment initiation within 3 to 6 seconds of application of the device to the skin.

Preferably, the threshold resistance value is a value less than the resistance of the particular body surface selected for drug delivery. A value between about 700 and about 800 kohms may be conveniently selected.

Commercially available electrotransport devices may be used in practicing the invention (for example, the Phoresor® device sold by Iomed, Inc. of Salt Lake City, Utah; the Dupel® system sold by Empi, Inc., St. Paul, Minn.; and the Webster sweat inducer sold by Wescor, Inc., Logan, Utah). These devices typically comprise a desk-top electrical power supply unit and a pair of skin contact electrodes (see, e.g., U.S. Pat. Nos. 4,141,359; 5,006,108). In addition, small self-contained electrotransport delivery devices adapted to be worn on the skin, may also be used (U.S. Pat. Nos. 5,224,927; 5,224,928; 5,246,418). The device may also comprise a reusable controller wherein the drug-containing unit is disconnected from the controller when the drug becomes depleted and a fresh drug-containing unit is thereafter connected to the controller (U.S. Pat. Nos. 5,320,597; 5,358,483; 5,135,479; UK Patent Application. 2 239 803). This results in an overall lowering of the cost of the device as the relatively more expensive hardware components can be contained within the reusable controller, and the relatively less expensive donor reservoir and counter reservoir matrices can be contained in the disposable drug containing unit.

An electrotransport system having a reusable controller may also be used wherein the power source in the reusable control unit is electrically disconnected from the current controlling circuit until the unit is ready for use, thus preserving battery strength and extending battery life (U.S. Pat. No. 5,562,607). The controller includes a power source and a circuit for controlling the timing, frequency, magnitude, etc. of the current applied by the device. The control circuit includes an internal circuit, such as a timing circuit, which at the time the device is in operation, is in contact with both poles of the battery through a circuit path other than the patient's body. A switch is provided for keeping the batteries electrically isolated from the closed internal circuit until the time when the device is placed in operation. The switch is closed automatically by coupling the disposable drug-containing unit to the reusable electronic controller. The switch is automatically reopened, and the battery(ies) again put in electrical isolation, when the drug-containing unit is uncoupled from the reusable controller.

The device may be rigid; flexible (U.S. Pat. No. 4,474, 570); or semi-rigid, i.e., a combination of rigid and flexible parts. A semi-rigid device may comprise two or more rigid regions, at least one of which is the drug delivery component, which are maintained in ion-transmitting relationship with the body surface at spaced apart locations, and which are held in their spaced apart locations by means of, for example, a biocompatible adhesive. Such devices further comprise a flexible connector which physically connects the rigid regions but which permits the rigid regions to move with respect to each other during agent electrotransport without loss of intimate contact with the surface of the patient's body. This connector may also be extendable, thereby allowing the zones (e.g., the electrodes) to be placed at closely adjacent locations, or more spaced apart locations on the patient's body. Such devices overcome the disadvantages of rigid devices, such as patient discomfort, while allowing incorporation of more complex electronic control circuitry than would otherwise be available using the entirely flexible devices.

Figure 2:
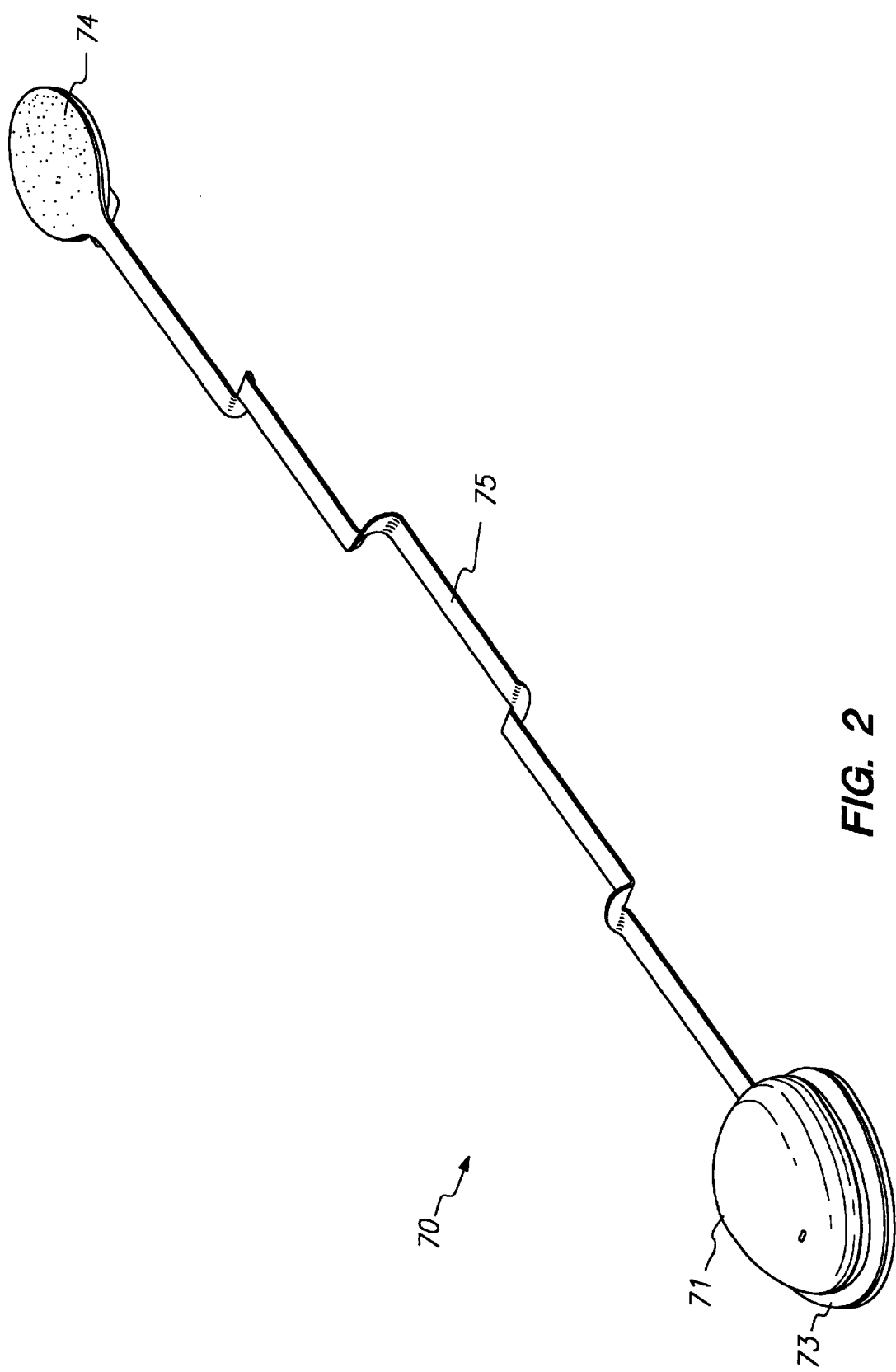
FIG. 2 is a perspective view of the device shown in FIG. 1 with the electrode assemblies in an extended configuration.

In a further modification, the semi-rigid device may comprise an isolatable power source, such as a reusable controller as described above. FIGS. 1–5 illustrate an example of such a device. Electrotransport device 70 comprises an electronic controller 71 and a single-use/disposable electrode unit 72. Electrode unit 72 comprises a donor electrode assembly 74 and a counter electrode assembly 73. The donor electrode assembly may be either rigid or non-rigid. The controller 71 is adapted to releasably engage electrode unit 72 by means of electrically conductive snap connectors 84, 85 as best shown in FIG. 4. Once the controller 71 engages snap connectors 84, 85, the combined assembly of controller 71 and counter electrode 73 comprises a rigid zone. As shown, electrode assemblies 73 and 74 are physically connected to one another by a flexible connector 75. Flexible connector 75 has a non-extended configuration (shown in FIG. 1) and an extended configuration (shown in FIG. 2). Thus, device 70 is manufactured with the flexible connector 75 having the non-extended serpentine configuration shown in FIG. 1. This configuration allows device 70 to be used on a patient with electrode assemblies 73 and 74 positioned closely adjacent to one another on the patient's body. However, electrode assemblies 73 and 74 may be placed at more distantly spaced locations on the patient's body by extending the flexible connector 75 as shown in FIG. 2. For example, it may be desirous to anesthetize a patients face prior to, for example, removal of a mole. The counter electrode assembly 73 can be placed at a body surface location other than on the patient's face, for example on the upper arm or shoulder, by pulling apart the electrode assemblies 73 and 74.

Figure 5:
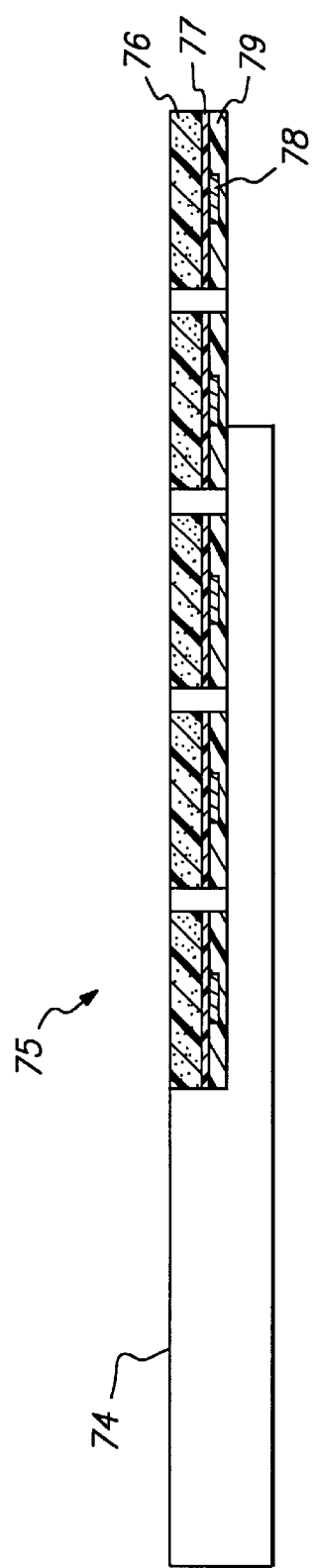
FIG. 5 is a sectional view of the device shown in FIGS. 1–4, taken along line V—V in FIG. 3.

In addition to physically connecting the electrode assemblies 73 and 74, the flexible connector 75 may comprise an electrically conductive circuit trace which electrically connects the donor electrode assemble 74 to the controller 71. FIG. 5 shows a sectional view of flexible connector 75 taken along lines XVIII—XVIII of FIG. 3. Flexible connector 75 comprises a multilaminate structure including a layer 76 of closed-cell polyolefin foam (e.g., polyethylene foam having a thickness of 0.8 mm (1/32 inch)(3M, St. Paul, Minn.) which is coated on one side with a pressure-sensitive (e.g., acrylate) adhesive. In addition to closedcll polyolefin foams, layer 76 can also be composed of fabric (woven or non-woven), or an elastomer (e.g., a rubber). On the adhesive coated face of layer 76 is laminated an ink-printable sheet 77, such as Mylar D polyester, having a thickness of 0.08 mm (3 mils)(E.I. DuPont DeNemours & Co., Wilmington, Del.). In addition to polyesters, sheet 77 can also be composed of polyolefins such as polyethylene, or polyvinylchloride. A continuous trace of electrically conductive ink 78 is printed on the polyester sheet 77. Suitable inks include silver, silver chloride and carbon based conductive inks. A particularly preferred ink is Model No. 478 SS (Acheson Colloids Co., Port Huron, Mich.). After printing conductive ink trace 78 on polyester sheet 77, the sheet 77 and trace 78 are coated with an insulating coating 79, providing insulation between the conductive ink trace 78 and the patient. Preferred insulative coating material are UV curable dielectric coatings such as ML-25094 and ML-25208 (Acheson Colloids).

As best shown in FIG. 4, the donor electrode assembly 74 is comprised of a foam layer 81 having a centrally positioned cavity holding a donor reservoir 82, in which the compositions are held. Similarly, counter electrode assembly 73 is comprised of a foam layer 83 having a centrally positioned cavity holding a counter reservoir 83. Preferably, reservoir 86 contains a solution of a biocompatible electrolyte.

The disposable electrode unit 72 is adapted to be physically and electrically connected to controller 71 by means of snap connectors 84 and 85. Snap connectors 84, 85 may be constructed of metal (e.g., stainless steel, nickel-coated brass or silver coated brass) or metal coated polymers (e.g., silver-coated ABS). Snap connector 85 electrically connects the counter electrode assembly 73 to the controller 71 whereas snap connector 84 electrically connects, through conductive ink trace 78, the donor electrode assembly 74 to the controller 71.

Controller 71 contains a pair of serially connected batteries 90 which provide the electrical power for device 70. Controller 71 includes a circuit board 91 having electrical components for controlling the timing and level of the applied current. Circuit board 91 includes an LED 92 which may be viewed through the opening 93 in the controller housing. The LED may be illuminated, for example, when the device in operation.

The invention will be further described by reference to the following detailed example.

EXAMPLE

Example I

Preparation and Stability of Iidocaine/Epinephrine Formulations

Two formulations were prepared to determine resistance to agent degradation. Formulas A and B comprised 2% lidocaine HCl (monohydrate) and 0.05% epinephrine, formula B additionally comprised 0.1% $Na_2S_2O_5$ and 0.1% EDTA.

A 15% PVOH solution was prepared as follows. A jacketed beaker was set up with water (90° C.) circulating through the jacket. Water (127.6 g, purified, $N_2$ bubbled for 30 min.) was added to the beaker. The stirrer was started, followed by the addition of 22.51 g polyvinyl alcohol (Hoechst 28-99). The beaker was covered with a teflon cover and the solution stirred for about 1 hr. The head space of the beaker was then flushed with $N_2$ for 5 minutes. The mixture was separated into 2×60 ml screwtop jars and the weights recorded (container A: 45.5975 g solution; container B: 47.7679 g solution).

A solution (solution 1) was prepared by dissolving 2.8125 g lidocaine $HCl°H_2O$ and 0.1033 g epinephrine bitartrate in 8.335 mL water in a 20 mL scintillation vial. The vial was wrapped with aluminum foil for light protection.

A second solution (solution 2) was prepared by dissolving 0.0775 g sodium metabisulfrte and 0.0770 g EDTA, disodium salt, dihydrate (Sigma) in 2.567 mL water in a 20 mL scintillation vial. The vial was wrapped with aluminum foil.

Formulation A was prepared by combining the contents of container A A 1 with 5.10 mL of solution 1 and 1.754 mL water. Formulation B was prepared by combining the container B with 5.30 mL of solution 1 and 1.838 mL of solution 2. The head spaces were flushed with $N_2$ and the containers wrapped with aluminum foil. The containers were mixed on a roller mixer until homogenous.

Calculation of the final formulations are presented in Table 1.

TABLE 1

|  | A | | B | |
| --- | --- | --- | --- | --- |
|  | % wt/wt | [mM] | % wt/wt | [mM] |
| PVOH | 13.03 |  | 13.05 |  |
| lidocaine base equivalent | 1.98 | 84.32 | 1.96 | 83.55 |
| epinephrine base equivalent | 0.049 | 2.68 | 0.049 | 2.66 |
| $Na_2S_2O_5$ |  |  | 0.095 | 5.01 |
| EDTA acid equivalent |  |  | 0.074 | 2.54 |

The formulations were packaged as follows: gel cavities were prepared (1.3 cm diameter×0.16 cm thick; 0.5 inch diameter×0.0625 inch thick) from two layers of 2-sided adhesive foam (0.79 cm thick; 0.03125 inch thick). 250 mL of formulation was dispensed into each cavity, and each side covered with a silicon coated release liner, and placed in a freezer (−20° C.) for 68 hr.

The foam housing was then cut into groups (n=3). Each group was placed into an appropriately labeled foil pouch, and the pouches heat sealed. The foil pouches for two samples (samples A2 and B2) were slit approximately 1 cm and the pouches filled with $N_2$ so that the pouch inflated. The pouches were then flattened to expel the $N_2$, and the procedure repeated twice. The slits were then heat sealed.

The samples were placed under various storage conditions as set forth in Table 2.

TABLE 2

| Time (wks) | storage temp (° C.) | samples | no. samples |
| --- | --- | --- | --- |
| 0 | 4 |  | 4 × 3 = 12 |
| 2 | 4, 25, 40 | A1, A2 | 4 × 3 × 3 = 36 |
| 4 | 4, 25, 40 | B1, B2 | 4 × 3 × 3 = 36 |

TABLE 2-continued

| Time (wks) | storage temp (° C.) | samples | no. samples |
| --- | --- | --- | --- |
| 8 | 4, 25, 40 |  | 4 × 3 × 3 = 36 |
| 16 | 4, 25, 40 |  | 4 × 3 × 3 = 36 |

Figure 7:
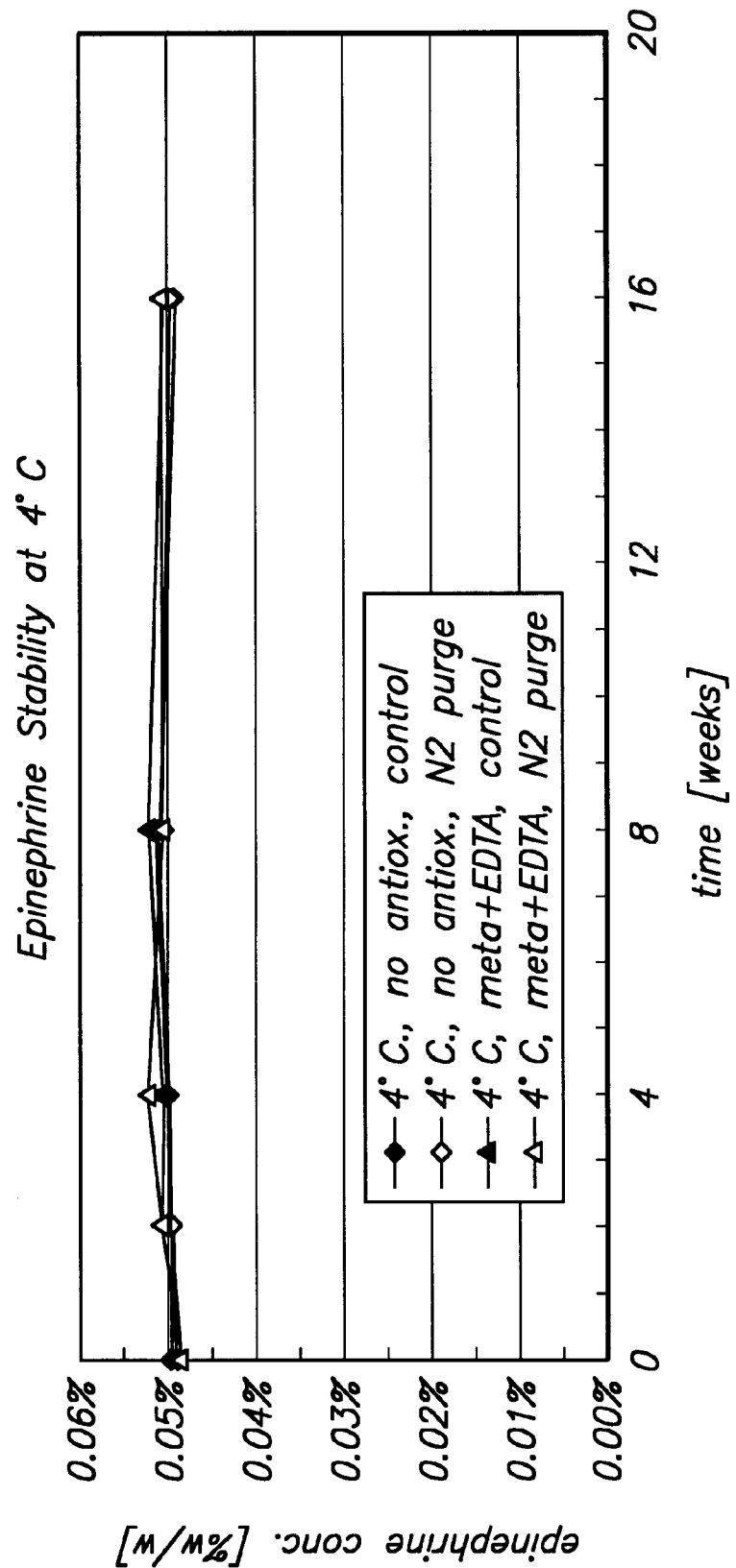
FIG. 7 shows the results of stability studies of certain formulations according to the invention at 4° C.
Figure 8:
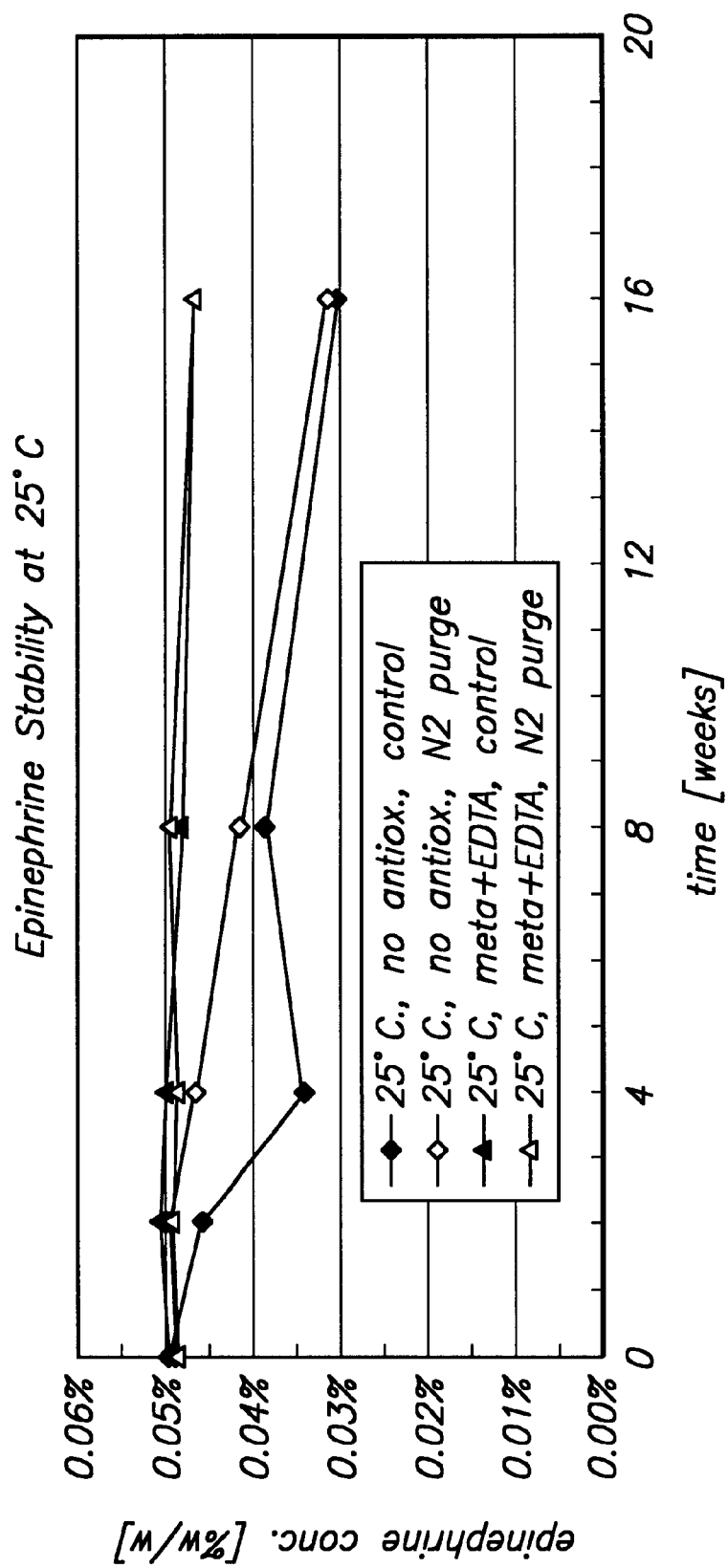
FIG. 8 shows the results of stability studies of certain formulations according to the invention at 25° C.
Figure 9:
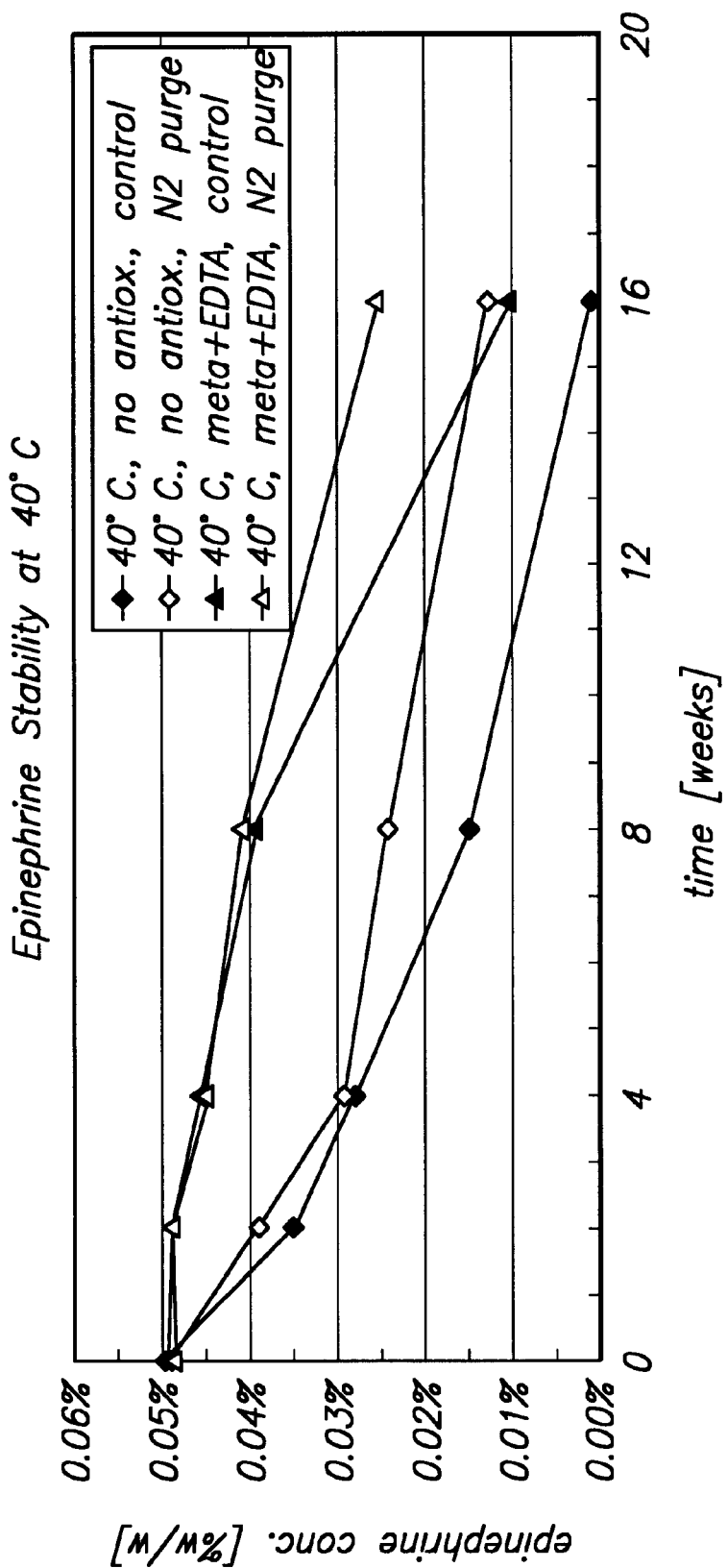
FIG. 9 shows the results of stability studies of certain formulations according to the invention at 40° C.

The results indicate that lidocaine does not degrade under any of the conditions tested. As shown in FIGS. 7, 8 and 9, the presence of antioxidants in the formulation reduces degradation of epinephrine. Purging the storage container with nitrogen helps to preserve epinephrine only at elevated temperatures beyond 8 weeks of storage. These results indicate that combining antioxidants in the formulation and storing the formulation in an inert environment provide the best conditions for maintaining epinephrine integrity.

All publications, patents and patent documents are incorporated by reference herein, as though individually incorporated by reference. The invention has been described with reference to various specific and preferred embodiments and techniques- However, it should be understood that many variations and modifications may be made while remaining within the spirit and scope of the invention.

What is claimed is:

1. An electrotransport delivery device for delivering an agent by electrotransport through a body surface, said device comprising:

a pair of electrode assemblies, at least one of the assemblies comprising the agent to be delivered;

a source of electrical power having a cell voltage and adapted to be electrically connected to said pair of electrode assemblies;

a controller which regulates electrical power between the power source and the electrode assemblies, said controller comprising an electrotransport current generating circuit which provides an output current to said pair of electrode assemblies and an activation circuit capable of detecting resistance between said electrode assemblies and said activating circuit capable of controlling the output current of the current generating circuit;

said current generating circuit capable of generating pulsed and non-pulsed output current and capable of providing said output current at a voltage both at or below the cell voltage and at a voltage greater than the cell voltage; and said activating circuit adapted to cause the current generating circuit to provide one or more pulses of output current at a voltage level greater than the cell voltage and said activating circuit adapted to detect resistance between said electrode assemblies any time during or after said pulses of output current, and when said detected resistance falls below a predetermined threshold value, said activating circuit causes the current generating circuit to generate a non-pulsed output current.

2. The device of claim 1, wherein the agent is a local anesthetics.

3. The device of claim 2, wherein the local anesthetic is lidocaine.

4. The device of claim 3 wherein the agent-containing electrode assembly further comprises epinephrine.

5. The device of claim 1 wherein the threshold resistance value is less than an initial resistance of the body surface.

6. The device of claim 5 wherein the threshold resistance is in a range of about 700 kohms to about 800 kohms.

7. The device of claim 1 wherein the voltage of said pulses is in a range of about 6 volts to about 24 volts.

8. The device of claim 1 wherein the non-pulsed output current is applied in a plurality of steps with each succeeding step having a voltage greater than the previous step.

9. A method of delivering an agent by electrotransport through body surface comprising the steps of:

applying a first electrode assembly to the body surface, said first electrode assembly comprising a reservoir containing the agent to be delivered;

applying a second electrode assembly to the body surface;

providing a battery as a source of electrical power, said battery having a cell voltage;

applying one or more pulsed voltages across the electrode assemblies, said pulsed voltage being greater than the cell voltage;

detecting resistance between said first and said second electrode assemblies any time during or after said pulses; and applying non-pulsed current between said first and said second electrode assemblies when the detected resistance falls below a predetermined threshold.

10. The method of claim 9 wherein the step of applying non-pulsed current is comprised of a plurality of steps in which the voltage of the non-pulsed current for the second step and any subsequent step is greater than the step before.

11. The method of claim 9 wherein the agent is lidocaine.

12. The method of claim 9 wherein said reservoir further comprises epinephrine.

13. The method of claim 9 wherein said body surface is a human body surface.

14. A method of delivering an agent by electrotransport through a body surface comprising the steps of:

providing a first and a second electrode assembly, at least one of the assemblies comprising the agent to be delivered;

providing a source of electrical power having a cell voltage and adapted to be electrically connected to said pair of electrode assemblies;

providing a controller which regulates electrical power between the power source and the electrode assemblies, said controller comprising an electrotransport current generating circuit which is capable of providing a pulsed and non-pulsed output current to said pair of electrode assemblies and an activation circuit capable of detecting resistance between said electrode assemblies and said activation circuit capable of controlling the output current of the current generating circuit;

applying the first electrode assembly to the body surface;

applying the second electrode assembly to the body surface;

causing the controller to apply one or more pulses of output current across the electrode assemblies, said output current pulses having a voltage greater than the cell voltage;

causing the activation circuit to detect resistance between said electrode assemblies any time during or after said pulses;

causing the controller to provide non-pulsed output current when the resistance detected by the activation circuit falls below a predetermined threshold.

15. The method of claim 14 wherein the step of applying non-pulsed current is comprised of a plurality of steps in which the voltage of the second step and any subsequent step is greater than the immediately preceding step.

16. The method of claim 14 wherein the agent is lidocaine.

17. The method of claim 14 wherein said reservoir further comprises epinephrine.

18. The method of claim 14 wherein said body surface is a human body surface.

* * * * *